United States Patent
Yoshida et al.

[11] Patent Number: 6,062,064
[45] Date of Patent: *May 16, 2000

[54] APPARATUS FOR SENSING LOW CONCENTRATION NOX

[75] Inventors: Toshihiro Yoshida; Naoyuki Ogawa, both of Nagoya; Tomonori Takahashi, Chita, all of Japan

[73] Assignee: NGK Insulators, Ltd., Nagoya, Japan

[ * ] Notice: This patent is subject to a terminal disclaimer.

[21] Appl. No.: 09/052,602

[22] Filed: Mar. 31, 1998

[30] Foreign Application Priority Data

Mar. 31, 1997 [JP] Japan .................................. 9-080054

[51] Int. Cl.[7] .................................................. G01N 27/04
[52] U.S. Cl. ............................................ 73/23.2; 436/118
[58] Field of Search ................................... 73/23.2, 23.21, 73/23.31, 31.06, 31.03; 422/90, 93; 436/110, 114, 117, 118

[56] References Cited

U.S. PATENT DOCUMENTS

| | | |
|---|---|---|
| 3,949,599 | 4/1976 | Kruishoop . |
| 4,315,753 | 2/1982 | Bruckenstein et al. . |
| 5,705,129 | 1/1998 | Takahashi et al. . |

FOREIGN PATENT DOCUMENTS

| | | |
|---|---|---|
| 0 467 307 | 1/1992 | European Pat. Off. . |
| 0 737 859 | 10/1996 | European Pat. Off. . |
| 0 874 236 | 10/1998 | European Pat. Off. . |
| 40 40 329 | 8/1992 | Germany . |
| 61-155848 | 7/1961 | Japan . |
| 63-250556 | 10/1988 | Japan . |
| 6222028 | of 1994 | Japan . |

*Primary Examiner*—Hezron Williams
*Assistant Examiner*—Michael Cygan
*Attorney, Agent, or Firm*—Wall Marjama Bilinski & Burr

[57] ABSTRACT

An apparatus for sensing low concentration NOx in the atmosphere is disclosed. The apparatus has sensor elements arranged in a flow path of the atmosphere, the resistance of each of said sensor elements varying in response to changes in NOx concentration of the atmosphere; a catalyst arranged between said sensor elements to maintain partial pressures of NO and $NO_2$ in the atmosphere at an equilibrium state; and measuring means for receiving signals from said sensor elements, one sensor element being contacted with the atmosphere which is not passed through said catalyst and the other sensor element being contacted with the atmosphere which is passed through said catalyst and for determining the concentrations of $NO_2$ and NO in the atmosphere on the basis of said signals.

15 Claims, 1 Drawing Sheet

APPARATUS FOR SENSING LOW CONCENTRATION NOX

BACKGROUND OF THE INVENTION

1. Field of the Invention

The present invention relates to an apparatus for sensing NOx in a gas to be measured, having a sensor element made of an oxide, the resistance of the oxide varying in response to changes in NOx concentration of the gas if the oxide is contacted with the gas including NOx, and a measuring portion for measuring a resistance variation of the sensor element and for determining an NOx concentration in the gas to be measured. The present invention especially relates to an apparatus used preferably for sensing low concentration NOx in the atmosphere as respective NO concentration and $NO_2$ concentration.

2. Related Art Statement

As a method of measuring an NOx concentration in a gas such as a fired gas from an incinerator, which includes an NOx component such as nitrogen oxide, it is known to sample the gas including an NOx component, in for example, a dust chimney, and to measure an NOx concentration of the sampled gas by means of an optical measuring apparatus. However, the optical measuring apparatus is expensive and the measurement time is long since the sampling operation is necessary.

In order to eliminate the drawbacks mentioned above, it has been proposed to use a direct insertion type semiconductor sensor. For example, in Japanese Patent Laid-Open Publication No. 6-222028 (JP-A-6-222028), an NOx sensor comprising a response portion made of an oxide having a predetermined perovskite structure, and a conductivity measuring portion for measuring a conductivity of the response portion is disclosed.

However, in the direct insertion type semiconductor sensor mentioned above, there is no countermeasure for an influence of $O_2$ and CO components included in the gas to be measured with respect to the measured NOx concentration. Moreover, in the response portion, the resistance thereof is varied in response to the concentration of NOx ($NO_2$+NO). However, if a ratio of partial pressure between $NO_2$ and NO, is varied, a resistance measured by the response portion is varied even for the same NOx amount. In this case, it is reasonable to conclude that the NOx component is not selectively measured. Therefore, in the direct insertion type semiconductor sensor mentioned above, there is a drawback in that the NOx concentration in the gas to be measured cannot be selectively measured in a highly precise manner, even though the semiconductor sensor is cheap and shows excellent response time as compared with the optical measuring apparatus.

Further, in order to solve the drawbacks mentioned above, the applicant discloses in U.S. Pat. No. 5,705,129 an NOx sensor comprising; an oxide sensor element; a catalyst arranged upstream of the oxide sensor element to maintain partial pressures of NO and $NO_2$ in the measurement gas at an equilibrium state; a heater for controlling a temperature of the oxide sensor element; and an $O_2$ sensor for a correction. However, also in the NOx sensor mentioned above, a target measurement gas is a fired exhaust gas from an incinerator as mentioned above. Therefore, the NOx sensor mentioned above cannot be used for measuring low concentration NOx in the atmosphere which is a target measurement gas of the invention.

SUMMARY OF THE INVENTION

An object of the present invention is to eliminate the drawbacks mentioned above and to provide an apparatus precisely for sensing low concentrations of NOx in the atmosphere as respective NO concentration and $NO_2$ concentration.

According to the invention, an apparatus for sensing low concentration NOx in the atmosphere, comprises; sensor elements arranged in a flow path of the atmosphere, the resistance of each of said sensor elements varying in response to changes in NOx concentration of the atmosphere; a catalyst arranged between said sensor elements to maintain partial pressures of NO and $NO_2$ in the atmosphere at an equilibrium state; and measuring means for receiving signals from said sensor elements, one sensor element being contacted with the atmosphere which is not passed through said catalyst and the other sensor element being contacted with the atmosphere which is passed through said catalyst and for determining the concentrations of $NO_2$ and NO in the atmosphere on the basis of said signals.

In the present invention, the catalyst to maintain partial pressures of NO and $NO_2$ in the atmosphere at an equilibrium state is used, and the sensor elements sense respectively the atmosphere which is not passed through the catalyst and the atmosphere which is passed through the catalyst. Then, NO concentration and $NO_2$ concentration are determined on the basis of the signals from the sensor elements. Therefore, it is possible to measure NO concentration and $NO_2$ concentration in the atmosphere in a highly precise manner.

DESCRIPTION OF THE PREFERRED EMBODIMENT

Figure 1:
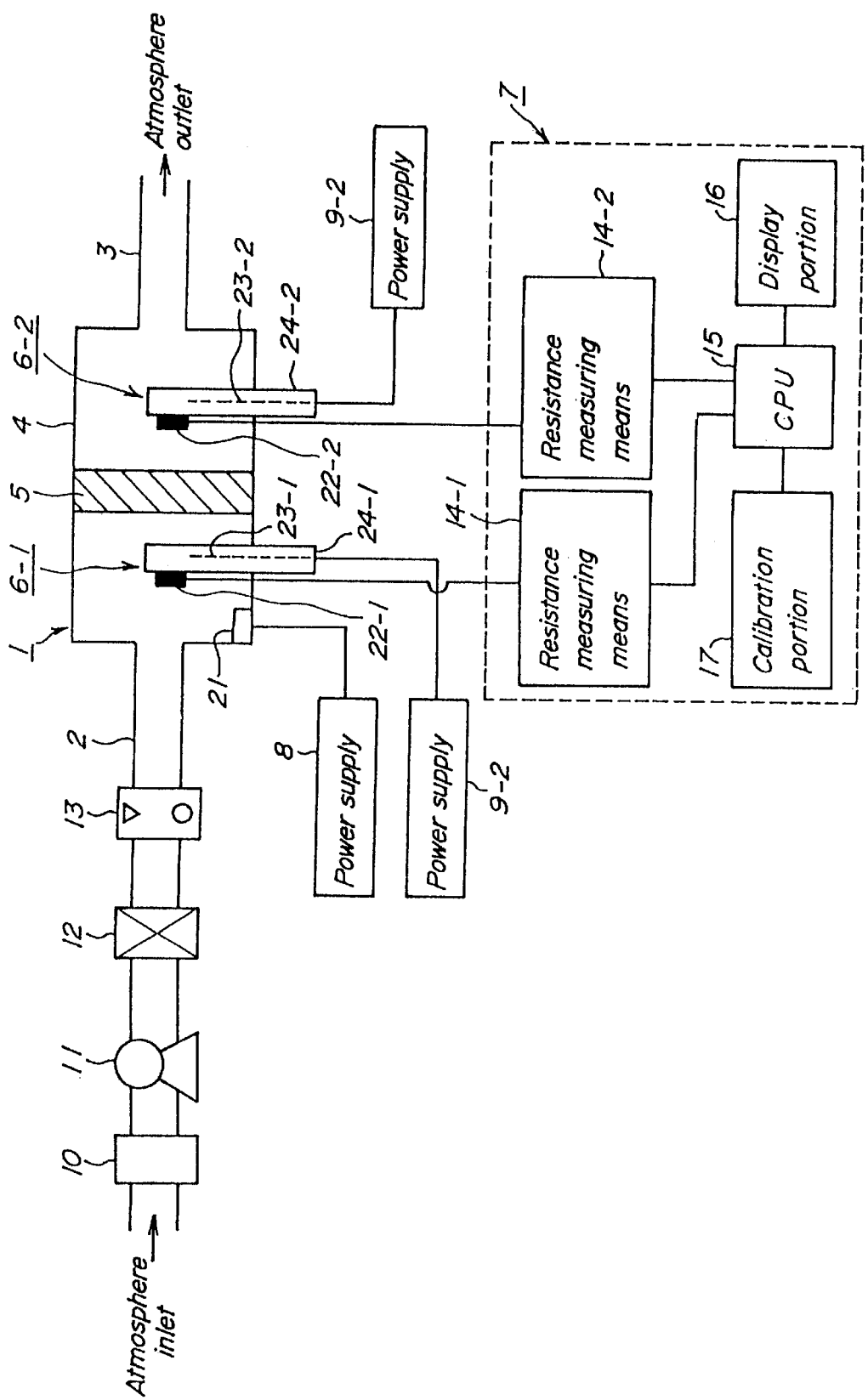
FIG. 1 is a schematic view showing one embodiment of an apparatus for sensing low concentration NOx according to the invention.

FIG. 1 is a schematic view showing one embodiment of an apparatus for sensing low concentration NOx according to the invention. In the embodiment shown in FIG. 1, an apparatus for sensing low concentration NOx 1 according to the invention is constructed. In particular, a sensor element 6-1, a catalyst 5, and a sensor element 6-2 are arranged in this order from an upstream side in a chamber 4 having an atmosphere inlet pipe 2 and an atmosphere outlet pipe 3. A measuring portion 7 is arranged outside of the chamber 4. Moreover, a a power supply 8 for heating the catalyst 5 by means of a heater 21, and power supplies 9-1 and 9-2 for heating the sensor elements, 6-1 and 6-2 respectively by means of heaters 23-1 and 23-2 are also provided. In the atmosphere inlet pipe 2, there are arranged, from an upstream side of an atmosphere flow, a filter 10 for removing foreign substances, a pump 11, a pressure reducing valve 12 and a flow meter 11, so that the atmosphere supplied in the chamber 4 always constant.

The measuring portion 7 comprises resistance measuring means 14-1 and 14-2 arranged correspondingly to the sensor elements 6-1 and 6-2, a CPU 15, a display portion 16 and a calibration portion 17. In the measuring portion 7, resistance variations of the sensor elements 6-1 and 6-2 are detected. As a result, the NO concentration and $NO_2$ concentration in the atmosphere are measured respectively by using a predetermined formula mentioned below on the basis of the thus detected resistance variations before and after passing the catalyst 5. In addition, the NOx concentration can be obtained from a sum of the thus measured NO concentration and $NO_2$ concentration.

The catalyst 5 is used for maintaining partial pressures of NO and $NO_2$ in the atmosphere at an equilibrium state, and for removing a combustible gas such as CO from the atmosphere by firing it. As a material of the catalyst 5, it is preferred to use a precious metal or a metal oxide. As a precious metal, it is preferred to use platinum, rhodium or gold. As a metal oxide, it is preferred to use manganese oxide, cobalt oxide or tin oxide. The catalyst 5 is heated by the heater 21 arranged in the chamber 4. Power is supplied to the heater 21 from the power supply 8.

In the sensor element 6-1 or 6-2, an oxide 22-1 or 22-2, whose resistance is varied in response to changes in NOx concentration of the atmosphere if it is contacted with the atmosphere, is arranged on a surface of a ceramic substrate 24-1 or 24-2. In this embodiment, the heater 23-1 or 23-2 is arranged in the ceramic substrate 24-1 or 24-2. Power is supplied to the heater 23-1 or 23-2 from the power supply 9-1 or 9-2. As the oxide 22-1 or 22-2, it is preferred to use a metal oxide semiconductor. As the metal oxide semiconductor, it is preferred to use $SnO_2$ or a mixture of $SnO_2$ and additives preferably consisting of Ta and Rh. Each of the sensor elements 6-1 and 6-2 has the same construction with each other. Using the oxide mentioned above for the sensor elements 6-1 and 6-2, makes it possible to use known features such as construction and shape, for the sensor elements 6-1 and 6-2.

Hereinafter, a method of measuring an NOx concentration in the atmosphere for sensing low concentration NOx having the construction mentioned above according to the invention will be explained. At first, temperatures T of the sensor elements 6-1 and 6-2 are respectively controlled by the power supplies 9-1 and 9-2 preferably in a range of 500° C.$\leq$T$\leq$800° C. In addition, a temperature of the catalyst 5 is controlled by the power supply 8 at a temperature of, for example, 380° C. at which the catalyst 5 can be activated. Under such a condition mentioned above, the atmosphere including NOx is supplied from the atmosphere inlet pipe 2 into the chamber 4. The thus supplied atmosphere is contacted with the sensor element 6-1 at first, and a resistance of the sensor element 6-1 is measured. Then, the atmosphere is passed through the catalyst 5, and partial pressures of NO and $NO_2$ (i.e. the $NO/NO_2$ ratio) in the atmosphere is maintained at an equilibrium state. Moreover, combustible substances such as CO are removed from the atmosphere. Then, the thus prepared atmosphere, in which the $NO/NO_2$ ratio is maintained at an equilibrium state and combustible substances are removed, is contacted with the sensor element 6-2, and the resistance of the sensor element 6-2 at that time is measured. A method of determining an NO concentration and an $NO_2$ concentration from the resistances of the atmosphere, before and after passing through the catalyst 5, which are measured by the sensor elements 6-1 and 6-2 will now be described.

Since an $NO/NO_2$ ratio of the atmosphere passing through the catalyst 5 is maintained at an equilibrium state, and further since an NOx partial pressure is a sum of an NO partial pressure and an $NO_2$ partial pressure, the following formulas (1) and (2) can be obtained.

$$P_{NO}/P_{NO2} = \alpha \quad (1)$$

$$P_{NO} + P_{NO2} + P_{NOX} \quad (2)$$

Moreover, as the applicant is previously disclosed, a relation between a resistance R and respective partial pressures of NO, $NO_2$ and $O_2$ can be obtained as the following formula (3).

$$\frac{1}{R} = Q - \frac{AP_{NO2} + BP_{NO} + CP_{O2}^{1/2} + DP_{NO}P_{O2}^{1/2}}{1 + EP_{NO2} + FP_{NO} + GP_{O2}^{1/2} + HP_{NO}P_{O2}^{1/2}} \quad (3)$$

wherein,

R: resistance,

A~H and Q: constant.

In this case, since a partial pressure of $O_2$ ($P_{O2}$) in the atmosphere is constant, it is possible to obtain a partial pressure of NOX ($P_{NOx}$) from the resistance R measured by the sensor element 6-2 on the basis of the formulas (1)–(3) the mentioned above. In the above formula (3), coefficients A–H and Q are previously determined for the sensor element 6-2 by using a gas in which NO, $NO_2$ and $O^2$ concentrations are known.

Further, it is possible to obtain a relation between a partial pressure of NO ($P_{NO}$) and a partial pressure of $NO_2$ ($P_{NO2}$) for the sensor element 6-1 from the above formula (3) by using the resistance R measured by the sensor element 6-1 for the atmosphere not passing through the catalyst 5 in which an $NO/NO_2$ ratio is varied. Also in this embodiment, coefficients A–H and Q of the formula (3) are previously determined for the sensor element 6-1 apart from those for the sensor element 6-2 by using a gas in which NO, $NO_2$ and $O_2$ concentrations are known. By solving simultaneous equations between the thus obtained relation of $P_{NO}$ and $P_{NO2}$ for the sensor element 6-1 and the above relation of the formula (2) for the sensor element 6-1 (here, $P_{NOx}$ is known), it is possible to obtain an NO concentration and an $NO_2$ concentration, respectively. In this case, $P_{NO}$ and $P_{NO2}$ are directly correspond to an NO concentration and an $NO_2$ concentration on the basis of previously prepared look-up tables showing a relation between $P_{NO}$ and an NO concentration, and a relation between $P_{NO2}$ and an $NO_2$ concentration.

A modification of the apparatus for sensing low concentration NOx according to the invention shown in FIG. 1 will now be explained. In the construction shown in FIG. 1, it is possible to arrange means for controlling temperatures of the catalyst 5 and the sensor elements 6-1 and 6-2 at a constant. The temperatures of the catalyst 5 and the sensor elements 6-1 and 6-2 are kept constant by arranging thermocouples in the catalyst 5 and the sensor elements 6-1 and 6-2, and by controlling the power supplies 8, 9-1 and 9-2 in response to changes in temperatures measured by those thermocouples. As an another embodiment, it is possible to keep temperatures of the catalyst 5 and the sensor elements 6-1 and 6-2 constant making a bridge circuit using Pt resistors as heaters 21, 2-1 and 23-2, and then controlling the temperatures of the catalyst 5 and the sensor elements 6-1 and 6-2 by responding to changes in the resistance of the Pt resistor.

Moreover, in the construction shown in FIG. 1, it is possible to arrange a water component control means to control the water component in the atmosphere at a constant in the atmosphere inlet pipe 2 arranged upstream of the chamber 4. As the water component control means, it is possible to use a freezer. In this case, it is preferred to control a dew point of the gas to be measured, which is set by the freezer, in a range of dew point ±0.2° C. As the freezer, it is preferred to use a freezer utilizing a peltier element based on Peltier effect, but other freezers such as a Perma Pure Dryer (product name) may be used for this purpose. In order to sense low concentration NOx in a highly precise manner, it is important to keep a water component amount in the atmosphere constant. Thus it is preferable to arrange a water component control means to control the water component in the atmosphere at a constant.

Further, in the construction shown in FIG. 1, it is possible to arrange a temperature detecting means proximate each of the sensor elements 6-1 and 6-2 so as to correct a resistance variation of each of the sensor elements 6-1 and 6-2 due to a temperature variation. In this case, an oxide whose resistance variation due to a temperature variation is the same as that of the sensor element 6-1 or 6-2 (e.g., an oxide having the same chemical composition as that of the oxide 22-1 or 22-2) is arranged on a surface of the ceramic substrate 24-1 or 24-2 opposed to the surface to which the oxide 22-1 or 22-2 is arranged. Then, a temperature variation of the sensor element 6-1 or 6-2 is measured by a temperature measuring portion arranged in the measuring portion 7 on the basis of the resistance variation of the thus arranged oxide. Then, it is possible to correct a resistance variation of the sensor element 6-1 or 6-2 in response to the thus measured temperature variation. In order to correct a resistance variation, the known correction method can be used. Moreover, it is possible to perform the same resistance variation correction by utilizing a thermocouple as the resistance detecting means. Further, it is possible to perform the same resistance variation correction by utilizing a resistance variation of the heater for heating the sensor element 6-1 or 6-2 as the temperature detecting means. In order to sense low concentration NOx in a highly precise manner, it is preferred to correct a resistance variation of the sensor element on the basis of a temperature variation of the sensor element as well as a water control operation.

Hereinafter, an actual experiment will be explained.

Experiment

NOx sensors according to examples 1–7 were prepared by varying the kind of oxide of a sensor element as shown in the following Table 1. In each example, the same sensor element was used for each sensor element 6-1 and 6-2. Manufacturing of the sensor element was performed as follows. At first, tin chloride was subjected to a hydrolysis by using an ammonia solution to obtain a dissolved solution. Then, the dissolved solution was separated by a filtering. After that, the thus separated dissolved solution was subjected to a pyrolysis at 600° C. for 2 hours to synthesize tin oxide powders. Then, the thus obtained tin oxide powders were mixed in a wet state in a mixed solution of acetone and diethylehexanol with organic binders and plasticizers for 10 hours by using zirconia balls. After that, acetone was vaporized to obtain a tin oxide slurry for a screen printing. As a substrate of the sensor element, use was made of an alumina plate having a dimension of 1×5×65 mm. Platinum electrodes and platinum heaters were previously screen-printed on the substrate, and the thus obtained tin oxide slurry was screen-printed on tip portions of the electrodes. The thus screen-printed substrate was fired at 800° C. for 2 hours to obtain a sensor element. In the case that Ta and Rh were included in the sensor element in a wet mixing operation, tantalum oxide and rhodium oxide were added with the organic binders. In this experiment, amounts of Ta and Rh were 3 at % with respect to Sn atoms respectively.

In the thus prepared NOx sensors according to the examples 1–7, a temperature of the sensor element, whether or not a temperature control was effected, whether or not a temperature correction was effected, and whether or not a water control was effected, were respectively set as shown in the following Table 1. Under such a condition, an NO concentration and an $NO_2$ concentration were measured in the manner mentioned above at 15 arbitrary points in the atmosphere, and an average value of data obtained for 1 hour was compared with a value measured according to an absorptiometry shown in JISB7953. An estimation was performed by comparing an inclination A and a correlation coefficient r of a regression curve with respect to the data measured by an absorptiometry. The results were shown in Table 1(a) and Table 1(b).

TABLE 1(a)

| | Example 1 | | | | Example 2 | | | | Example 3 | | | | Example 4 | | | |
|---|---|---|---|---|---|---|---|---|---|---|---|---|---|---|---|---|
| Element | $SnO_2$ | | | | $SnO_2$ | | | | $SnO_2$ | | | | $SnO_2$ + Ta + Rh | | | |
| Catalyst | Pt | | | | Pt | | | | Pt | | | | Pt | | | |
| Temperature | 520° C. | | | | 500° C. | | | | 800° C. | | | | 520° C. | | | |
| Temperature control | none | | | | none | | | | none | | | | none | | | |
| Temperature correction | none | | | | none | | | | none | | | | none | | | |
| Water control | none | | | | none | | | | none | | | | none | | | |
| Concentration (ppb) | absorptiometry | | present invention | | absorptiometry | | present invetion | | absorptiometry | | present invention | | absorptiometry | | present invention | |
| | $NO_2$ | NO | $NO_2$ | NO | $NO_2$ | NO | $NO_2$ | NO | $NO_2$ | NO | $NO_2$ | NO | $NO_2$ | NO | $NO_2$ | NO |
| | 32 | 21 | 28 | 19 | 28 | 19 | 32 | 21 | 32 | 21 | 28 | 19 | 7 | 4 | 9 | 6 |
| | 72 | 48 | 69 | 46 | 48 | 32 | 45 | 30 | 70 | 47 | 66 | 44 | 29 | 19 | 31 | 20 |
| | 15 | 40 | 12 | 8 | 19 | 12 | 21 | 14 | 15 | 10 | 11 | 7 | 30 | 20 | 27 | 18 |
| | 18 | 12 | 21 | 14 | 32 | 21 | 28 | 19 | 17 | 11 | 21 | 14 | 48 | 32 | 50 | 33 |
| | 30 | 20 | 34 | 23 | 72 | 48 | 67 | 44 | 33 | 22 | 33 | 22 | 22 | 14 | 25 | 16 |
| | 47 | 31 | 48 | 33 | 15 | 10 | 12 | 8 | 84 | 56 | 82 | 54 | 33 | 22 | 31 | 21 |
| | 54 | 36 | 52 | 34 | 54 | 36 | 51 | 34 | 30 | 20 | 30 | 20 | 81 | 54 | 79 | 52 |
| | 28 | 19 | 32 | 21 | 33 | 22 | 30 | 20 | 48 | 32 | 50 | 33 | 30 | 20 | 32 | 21 |
| | 48 | 32 | 45 | 30 | 81 | 54 | 79 | 52 | 22 | 14 | 25 | 16 | 47 | 31 | 51 | 34 |
| | 19 | 12 | 21 | 14 | 30 | 20 | 32 | 21 | 33 | 22 | 30 | 20 | 43 | 29 | 44 | 29 |
| | 39 | 26 | 34 | 23 | 40 | 26 | 34 | 23 | 39 | 25 | 34 | 22 | 48 | 32 | 49 | 33 |
| | 89 | 59 | 85 | 56 | 89 | 58 | 85 | 56 | 90 | 60 | 84 | 56 | 52 | 34 | 55 | 37 |
| | 13 | 5 | 16 | 10 | 12 | 8 | 16 | 11 | 13 | 8 | 16 | 11 | 54 | 36 | 50 | 33 |
| | 51 | 34 | 54 | 36 | 39 | 26 | 34 | 23 | 56 | 37 | 54 | 36 | 60 | 40 | 62 | 41 |

TABLE 1(a)-continued

|  | Example 1 | | | | Example 2 | | | | Example 3 | | | | Example 4 | | | |
| --- | --- | --- | --- | --- | --- | --- | --- | --- | --- | --- | --- | --- | --- | --- | --- | --- |
|  | 60 | 40 | 56 | 37 | 50 | 40 | 55 | 37 | 26 | 17 | 24 | 16 | 39 | 26 | 36 | 24 |
|  | 33 | 22 | 28 | 19 | 33 | 22 | 25 | 17 | 33 | 2 | 28 | 19 | 90 | 50 | 85 | 57 |
| Inclination A | 0.927 | 0.917 | | | 0.934 | 0.918 | | | 0.937 | 0.923 | | | 0.941 | 0.934 | | |
| Correlation coefficient r | 0.988 | 0.988 | | | 0.99 | 0.991 | | | 0.992 | 0.991 | | | 0.992 | 0.991 | | |

TABLE 1(b)

|  | Example 5 | | | | Example 6 | | | | Example 7 | | | |
| --- | --- | --- | --- | --- | --- | --- | --- | --- | --- | --- | --- | --- |
| Element | $SnO_2$ + Ta + Rh | | | | $SnO_2$ + Ta + Rh | | | | $SnO_2$ + Ta + Rh | | | |
| Catalyst | Pt | | | | Pt | | | | Pt | | | |
| Temperature | 520° C. | | | | 520° C. | | | | 520° C. | | | |
| Temperature control | effect | | | | effect | | | | effect | | | |
| Temperature correction | none | | | | none | | | | effect | | | |
| Water control | none | | | | effect | | | | effect | | | |
| Concentration (ppb) | absorptiometry | | present invention | | absorptiometry | | present invention | | absorptiometry | | present invention | |
|  | $NO_2$ | NO | $NO_2$ | NO | $NO_2$ | NO | $NO_2$ | NO | $NO_2$ | NO | $NO_2$ | NO |
|  | 10 | 7 | 8 | 5 | 37 | 25 | 37 | 24 | 29 | 19 | 31 | 20 |
|  | 36 | 24 | 31 | 20 | 29 | 19 | 27 | 18 | 30 | 20 | 29 | 19 |
|  | 97 | 64 | 96 | 64 | 13 | 9 | 14 | 9 | 48 | 32 | 49 | 32 |
|  | 54 | 36 | 55 | 37 | 52 | 34 | 53 | 35 | 52 | 34 | 54 | 36 |
|  | 30 | 20 | 31 | 21 | 27 | 18 | 29 | 19 | 34 | 22 | 36 | 24 |
|  | 31 | 21 | 33 | 22 | 33 | 22 | 33 | 22 | 58 | 38 | 61 | 41 |
|  | 40 | 27 | 42 | 28 | 84 | 56 | 82 | 54 | 84 | 56 | 85 | 57 |
|  | 42 | 28 | 39 | 26 | 30 | 20 | 30 | 20 | 30 | 20 | 32 | 21 |
|  | 13 | 8 | 12 | 8 | 56 | 37 | 54 | 36 | 36 | 24 | 33 | 22 |
|  | 77 | 51 | 72 | 48 | 26 | 17 | 24 | 16 | 97 | 64 | 96 | 64 |
|  | 88 | 58 | 84 | 56 | 40 | 26 | 39 | 26 | 54 | 36 | 55 | 37 |
|  | 33 | 22 | 38 | 25 | 54 | 36 | 54 | 36 | 30 | 20 | 31 | 20 |
|  | 49 | 33 | 51 | 34 | 97 | 65 | 94 | 63 | 30 | 20 | 30 | 20 |
|  | 14 | 9 | 16 | 10 | 61 | 40 | 61 | 41 | 29 | 19 | 28 | 19 |
|  | 39 | 26 | 40 | 26 | 24 | 16 | 25 | 17 | 13 | 9 | 14 | 9 |
|  | 55 | 36 | 54 | 36 | 46 | 31 | 49 | 32 | 52 | 34 | 53 | 35 |
| Inclination A | 0.958 | 0.975 | | | 0.965 | 0.967 | | | 0.999 | 1.019 | | |
| Correlation coefficient r | 0.994 | 0.994 | | | 0.998 | 0.998 | | | 0.998 | 0.997 | | |

From the results shown in Table 1 (a) and Table 1 (b), it is understood that the NO and $NO_2$ concentrations of the examples 1–7 measured according to the invention are identical with those measured by an absorptiometry. Thus it is possible to measure an NO concentration and an $NO_2$ concentration in a highly precise manner. Moreover, it is understood that, among the data of the examples 1–7, the examples in to which a temperature control and/or a temperature correction and/or a water control are effected, result in more precise measurements of NO concentration and $NO_2$ concentration as compared with thee example, to which no temperature control, a temperature correction, or a water control are effected.

As clearly understood from the explanations mentioned above, since the sensor elements sense respectively the atmospheres before and after passing through the catalyst for maintaining partial pressures of NO and $NO_2$ in the atmosphere at an equilibrium state, (preferably the atmospheres before and after passing through the catalyst in which a temperature T of the sensor element is maintained in a range of 500° C.$\leq$T$\leq$800° C. and a temperature control, a temperature correction and/or a water control are effected) it is possible to measure an NO concentration and an $NO_2$ concentration in the atmosphere in a highly precise manner.

While the present invention has been described with reference to the particular embodiment outlined above, it will be understood that various changes could be made without departing from the spirit and scope of the invention as defined in the claims. For example, while it is preferred that the gas flow pass through the catalyst, it is possible for the gas flow to simply contact the catalyst (e.g., the catalyst could be arranged on one side of a pipe through which the gas flows). Additionally, the two sensors could be arranged in two separate gas flow conduits, with the catalyst arranged in one of the two conduits.

What is claimed is:

1. An apparatus for sensing low concentration NOx in the atmosphere, comprising;

sensor elements arranged in a flow path of the atmosphere, the resistance of each of said sensor elements varying in response to changes in NOx concentration of the atmosphere;

a catalyst arranged to maintain partial pressures of NO and $NO_2$ in the atmosphere at an equilibrium state; and measuring means for receiving signals from said sensor elements, one sensor element being contacted with the atmosphere which is not contacted with said catalyst and the other sensor element being contacted with the atmosphere which is contacted with said catalyst and for determining the concentrations of $NO_2$ and NO in the atmosphere on the basis of said signals.

2. The apparatus according to claim 1, wherein a temperature T of each of said sensor elements is maintained in a range of 500° C.$\leq$T$\leq$800° C.

3. The apparatus according to claim 1, wherein said sensor elements comprise a metal oxide semiconductor.

4. The apparatus according to claim 3, wherein said metal oxide semiconductor is made of $SnO_2$ or a mixture of $SnO_2$ and additives.

5. The apparatus according to claim 4, wherein said additives are Ta and Rh.

6. The apparatus according to claim 1, wherein said catalyst comprises one of a precious metal and a metal oxide.

7. The apparatus according to claim 1, further comprising temperature detecting means arranged proximate each of said sensor elements to correct a resistance variation of each of said sensor elements due to a temperature variation.

8. The apparatus according to claim 7, wherein said temperature detecting means comprise an oxide, the resistance variation of said oxide being same as that of each of said sensor elements.

9. The apparatus according to claim 7, wherein said temperature detecting means comprise a thermocouple.

10. The apparatus according to claim 7, wherein said temperature detecting means comprise a Pt resistance heater for heating each of said sensor elements.

11. The apparatus according to claim 1, further comprising temperature control means for maintaining temperatures of said sensor elements and said catalyst at a constant state.

12. The apparatus according to claim 1, further comprising water component control means arranged upstream of each of said sensor elements to maintain a water component in the atmosphere at a constant state.

13. The apparatus according to claim 1, wherein said catalyst is arranged between said sensor elements.

14. The apparatus according to claim 1, wherein said flow path includes two branches, and one of said sensor elements and said catalyst are arranged in a first branch and the other one of said sensor elements is arranged in a second branch.

15. The apparatus according to claim 1, wherein the atmosphere flows through said catalyst.

* * * * *